(12) United States Patent
Kiraly et al.

(10) Patent No.: US 7,583,829 B2
(45) Date of Patent: Sep. 1, 2009

(54) METHOD AND APPARATUS FOR EMBOLISM ANALYSIS

(75) Inventors: Atilla Peter Kiraly, Plainsboro, NJ (US); Carol L. Novak, Newtown, PA (US); Lutz Gündel, Erlangen (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 718 days.

(21) Appl. No.: 11/202,801

(22) Filed: Aug. 12, 2005

(65) Prior Publication Data

US 2006/0056685 A1    Mar. 16, 2006

Related U.S. Application Data

(60) Provisional application No. 60/609,521, filed on Sep. 13, 2004.

(51) Int. Cl.
    *G06K 9/00*    (2006.01)
(52) U.S. Cl. .................. 382/128; 382/131; 382/132
(58) Field of Classification Search .............. 382/128, 382/132; 128/922
    See application file for complete search history.

(56) References Cited

U.S. PATENT DOCUMENTS

| | | | | |
|---|---|---|---|---|
| 5,734,384 | A * | 3/1998 | Yanof et al. ............... | 345/424 |
| 5,872,861 | A * | 2/1999 | Makram-Ebeid ............ | 382/130 |
| 6,083,162 | A * | 7/2000 | Vining ......................... | 600/407 |
| 6,501,848 | B1 * | 12/2002 | Carroll et al. ................ | 382/128 |
| 6,577,752 | B2 * | 6/2003 | Armato et al. ............... | 382/131 |
| 7,194,117 | B2 * | 3/2007 | Kaufman et al. ............ | 382/128 |
| 7,203,353 | B2 * | 4/2007 | Klotz et al. .................. | 382/131 |
| 7,272,250 | B2 * | 9/2007 | Schneider et al. ........... | 382/128 |
| 7,315,639 | B2 * | 1/2008 | Kuhnigk ...................... | 382/131 |
| 7,379,572 | B2 * | 5/2008 | Yoshida et al. .............. | 382/128 |
| 2002/0009215 | A1 * | 1/2002 | Armato et al. .............. | 382/131 |
| 2004/0258296 | A1 * | 12/2004 | Bruijns ........................ | 382/154 |

(Continued)

OTHER PUBLICATIONS

Kiraly et al. "3D human airway segmentation for virtual bronchoscopy", Proceedings of SPIE vol. 4683, 2002, pp. 16-29.*

(Continued)

*Primary Examiner*—Samir A. Ahmed
*Assistant Examiner*—Li Liu

(57) ABSTRACT

Disclosed is an automated technique for analyzing the affected region due to an embolism in an organ. A segmented image of the organ vasculature is generated using image volume data received, for example, from a Computed Tomography (CT) machine. An embolus is then identified (either manually or automatically) within the segmented image, and the volume of the organ affected by the embolism is automatically determined. The volume of the organ affected by the embolism may be determined by computing a sub-tree within the segmented image, where the sub-tree comprises vessels that are distal to the identified embolus point. In one embodiment, the sub-tree is generated by determining a plane perpendicular to a vessel at the embolus point such that the sub-tree comprises a distal portion of the vasculature with respect to the plane. Unwanted overlapping trees are identified (e.g., by analyzing branch angles) and removed from the sub-tree. The volume of the organ affected by the embolism is determined by calculating a volume of the organ that is perfused by the sub-tree. The affected volume may be adjusted by scaling the volume based on the percentage occlusion of the partial embolus.

34 Claims, 10 Drawing Sheets

U.S. PATENT DOCUMENTS

2006/0056691 A1* 3/2006 Vaz et al. ............... 382/173

OTHER PUBLICATIONS

Wildberger et al. "Multi-slice CT for visualization of pulmonary embolism using perfusion weighted color maps". Fortschr Rontgenstr Apr. 2001; 173(4): 289-294.*

Ishikawa et al. "Evolution of cerebral ischaemia induced by thromboembolism in rats detected by early sequential MR imaging", Br J Anaesth 2001; 87: 469-76.*

Talbot et al. "Image analysis of insulation mineral fibres." J Microsc. Dec. 2000; 200(Pt 3): 251-268.*

P. Herzog, et al., "CT Perfusion Imaging of the Lung in Pulmonary Embolism", Academic Radiology, vol. 10, No. 10, pp. 1132-1146, Oct. 2003.

M. Remy-Jardin, et al., "Diagnosis of Pulmonary Embolism with Spiral CT: Comparison with Pulmonary Angiography & Scintigraphy", Radiology, vol. 200, No. 3, pp. 699-706, Sep. 1996.

K. Kim, et al., "Clinically Suspected Pulmonary Embolism: Utility of Spiral CT", Radiology, vol. 210, No. 3, pp. 693-697, Mar. 1999.

A.P. Kiraly, et al., "Three-Dimensional Path Planning for Virtual Bronchoscopy", IEEE Transactions on Medical Imaging, vol. 23, No. 9, pp. 1365-1379, Sep. 2004.

Y. Masutani, et al., "Computerized Detection of Pulmonary Embolism in Spiral CT Angiography Based on Volumetric Image Analysis", IEEE Transactions on Medical Imaging vol. 21, No. 12, pp. 1517-1523, Dec. 2002.

J. Mayo, et al. "Pulmonary Embolism: Prospective Comparison of Spiral CT with Ventilation-Perfusion Scintigraphy", Radiology 1997, 205 447-452..

E. Pichon, et al., "A Novel Method for Pulmonary Emboli Visualization from High-Resolution CT Images", Proceedings of the SPIE Medical Imaging 2004, vol. 5367, pp. 161-170 (2004).

Y. Sato, et al., "Three-Dimensional Multi-Scale Line Filter for Segmentation and Visualization of Curvilinear Structures in Medical Images", Medical Image Analysis (1998), vol. 2, No. 2 pp. 143-168.

U. Schoepf, et al., "Subsegmental Pulmonary Emboli: Improved Detection with Thin-Collimation Multi-Detector Row Spiral CT", Radiology 2002, vol. 222, No. 2, pp. 483-490.

C. Zhou, et al., "Computerized Detection of Pulmonary Embolism in 3D Computed Tomographic (CT) Images: Vessel Tracking and Segmentation Techniques", Proceedings of SPIE, vol. 5032, pp. 1613-1620 (2003).

A.P. Kiraly, et al., "Analysis of Branching Tubular Structures in 3D Digital Images", Proceedings International Conference on Image Processing (2002), IEEE Press, vol. 2, pp. 333-336.

* cited by examiner

1002

AFFECTED REGION: 5.7%

METHOD AND APPARATUS FOR EMBOLISM ANALYSIS

This application claims the benefit of U.S. Provisional Application No. 60/609,521 filed Sep. 13, 2004, which is incorporated herein by reference.

BACKGROUND OF THE INVENTION

The present invention relates generally to analysis of emboli, and more particularly to automatically analyzing the affected region due to an embolism in an organ.

Embolism is the obstruction of a blood vessel by a foreign substance. Blood clots are the most common cause of embolism. A pulmonary embolus is a blood clot that has been carried through the blood stream into a pulmonary artery (blood vessels proceeding from the heart into the lungs) partially or fully blocking that vessel. The term "embolus" refers to the plug obstructing the blood vessel while embolism refers to the process by which this happens.

Although Pulmonary Embolism (PE) is a common causes of unexpected death, it may often be preventable. Prompt treatment with anti-coagulants is essential to prevent loss of life. However, treatments also carry risks, so correct diagnosis is critical. Computed tomography angiography (CTA) is gaining increasing acceptance as a method of diagnosis, offering sensitivity and specificity comparable or superior to alternative methods such as pulmonary angiography and ventilation-perfusion scans. CTA is rapid and non-invasive, and in many cases has the benefit of allowing an alternative diagnosis to explain a patient's symptoms.

Images acquired from 16-slice Computed Tomography (CT) machines of contrast-injected patients provide very high-resolution data, allowing for better detection of emboli located in sub-segmental arteries. This high resolution three dimensional data offers the potential for precise analysis of the effects of PEs on the lungs, but such assessments may be infeasible without automation.

Current techniques for automated analysis of PE within contrast-enhanced CT images relate to the direct detection of the clots themselves within the arteries, or indirect inference of clot location by visualization of perfusion defects in affected lung area(s). In the former case, a good segmentation of the arteries is generally required in order to detect the precise locations of PEs. Detection of clots can then be done through a visualization technique or through Computer Aided Detection (CAD).

In another technique for automated analysis of CTA, the mean density of local areas of the lungs are computed and rendered to directly visualize perfusion defects. Lung areas showing lower than average density may be suggestive of an upstream clot. An advantage of this technique is that it gives a graphical representation of the extent and severity of the disease. However a disadvantage is that in order to properly measure perfusion, two scans are required, before and after contrast, requiring a complicated acquisition and twice as much radiation. In addition, non-rigid registration is required to align the two scans, which is difficult and time-consuming. Currently the accepted clinical practice for evaluating patients with possible PE is to perform only a single post-contrast scan.

Therefore, what is needed is an automated technique for analyzing from a single scan the extent to which embolism affects an organ.

BRIEF SUMMARY OF THE INVENTION

The present invention provides an automated technique for analyzing the affected region due to an embolism in an organ. In accordance with an embodiment of the invention, a segmented image of the organ vasculature is generated using image volume data received, for example, from a Computed Tomography (CT) machine. An embolus is then identified within the segmented image. The embolus may be identified by receiving the embolus point as input (e.g., where the embolus point is manually identified). Alternatively, the embolus point may be identified automatically. Based on this data, the volume of the organ affected by the embolism is automatically determined.

The volume of the organ affected by the embolism may be determined by computing a sub-tree within the segmented image, where the sub-tree comprises vessels that are distal to the identified embolus point. In one embodiment, the sub-tree is generated by determining a plane perpendicular to a vessel at the embolus point such that the sub-tree comprises a distal portion of the vasculature with respect to the plane. Since the sub-tree image may contain unwanted overlapping trees, such overlapping trees are identified (e.g., by analyzing branch angles) and removed from the sub-tree. At this point, the volume of the organ affected by the embolism may be determined by calculating a volume of the organ that is perfused by the sub-tree. Further, since the embolism may only cause a partial blockage of an artery, affected volume may be adjusted by scaling the volume based on the percentage occlusion of the partial embolus. Further, since there may be more than one embolus in a patient, the process may be iterated by identifying additional emboli, calculating the percentage of the organ perfused by each sub-tree, and summing these together to get a total percentage of the organ affected by all emboli.

These and other advantages of the invention will be apparent to those of ordinary skill in the art by reference to the following detailed description and the accompanying drawings.

DETAILED DESCRIPTION

Figure 1:
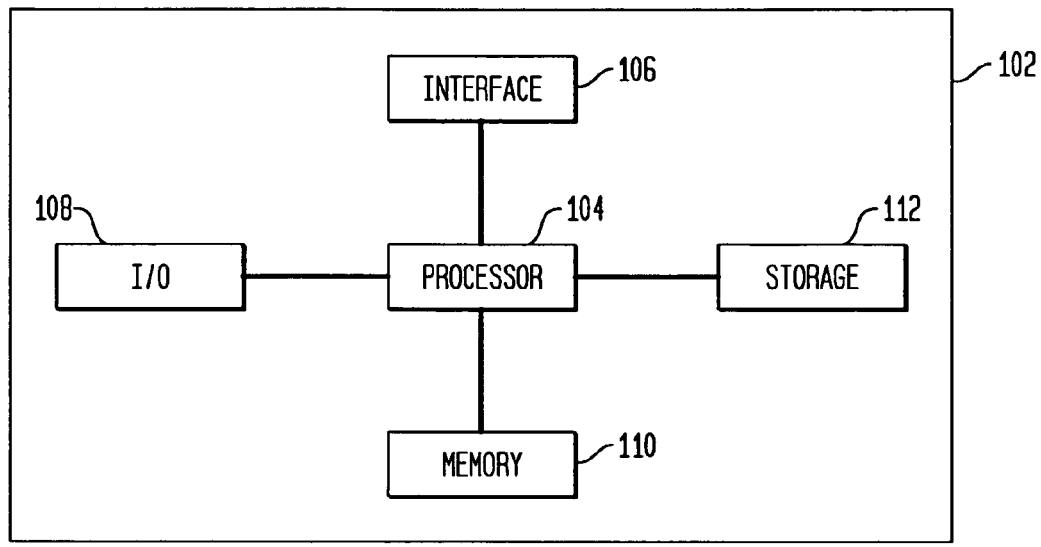
FIG. 1 is a high level block diagram of a computer in which the present invention may be implemented.

The following description describes the present invention in terms of the processing steps required to implement an embodiment of the invention. These steps may be performed by an appropriately programmed computer, the configuration of which is well known in the art. An appropriate computer may be implemented, for example, using a well known computer processors, memory units, storage devices, computer software, and other components. A high level block diagram of such a computer is shown in FIG. 1. Computer 102 contains a processor 104 which controls the overall operation of computer 102 by executing computer program instructions which define such operation. The computer program instructions may be stored in a storage device 112 (e.g., magnetic disk) and loaded into memory 110 when execution of the computer program instructions is desired. Computer 102 also includes one or more interfaces 106 for communicating with other devices (e.g., locally or via a network). Computer 102 also includes input/output 108 which represents devices which allow for user interaction with the computer 102 (e.g., display, keyboard, mouse, speakers, buttons, etc.). One skilled in the art will recognize that an implementation of an actual computer will contain other components as well, and that FIG. 1 is a high level representation of some of the components of such a computer for illustrative purposes. In addition, one skilled in the art will recognize that the processing steps described herein may also be implemented using dedicated hardware, the circuitry of which is configured specifically for implementing such processing steps. Alternatively, the processing steps may be implemented using various combinations of hardware and software.

Figure 2:
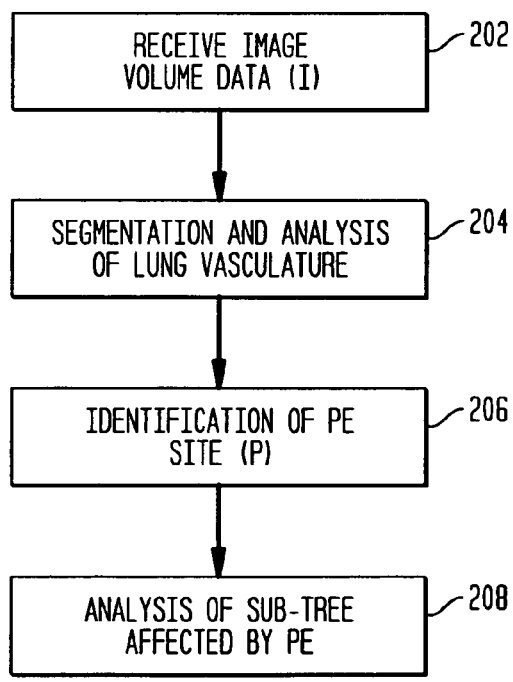
FIG. 2 is a flowchart of the steps performed in accordance with an embodiment of the invention.

FIG. 2 shows a flowchart of the steps performed in accordance with an embodiment of the invention. Initially a brief overview of the steps will be given. Further details regarding each of the steps of FIG. 2 will be provided following the general description. First, in step 202, image volume (I) data is received. After receipt of the image volume data in step 202, segmentation and analysis of the lung vasculature is performed in step 204. Next, in step 206, the PE site within the segmented lung vasculature is identified. This identification of a PE site may be input manually after examination of an image of the segmented lung vasculature, or the PE site may be automatically identified. In step 208 the vascular sub-tree affected by the PE is analyzed to determine a volume of the lung affected by the PE.

Further details of steps of FIG. 2 will now be described in further detail using the following notation. The original image volume is represented by I. The selected PE site is given by p=(x, y, z), where (x, y, z) represents the 3 dimensional coordinates of the PE site. The volume containing the segmented vasculature within the lung is referred to as S. Finally, the segmented sub-tree volume is referred to as S'.

Step 202 represents the image volume data as an input to the processing steps. In an advantageous embodiment, this image volume data represents images acquired by a multi-slice Computed Tomography (CT) machine of a contrast injected patient. This data may be received, for example, via a connection (e.g., direct or via network) to the CT machine via interface 106, or via a removable data storage device (e.g., CD ROM, magnetic disk, flash memory, or any other type of removable data storage device). Alternatively, the present invention may be implemented as an integrated system within a CT machine, in which case the processing described herein would be performed within the CT machine itself.

Figure 3:
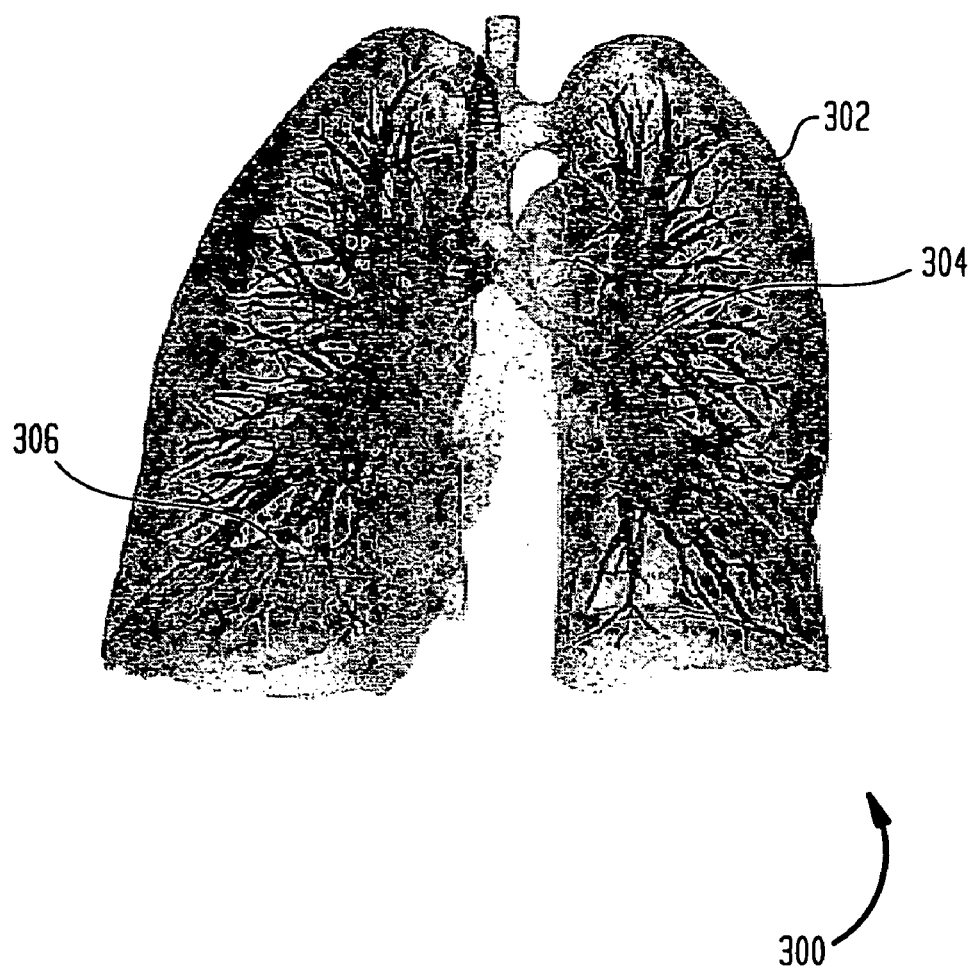
FIG. 3 shows a segmentation of the pulmonary vasculature S.

In step 204, segmentation and characterization of the lung vasculature is performed. In one embodiment, this step is performed as described in Pichon E, Novak C L, Kiraly A P, Naidich D P, "A novel method for pulmonary emboli visualization from high-resolution CT images," Proceedings of the SPIE Medical Imaging 2004, Volume 5367, p. 161-170 (2004), which is incorporated herein by reference. This technique proceeds as follows. First, a mask of the lungs is created. A seed point is initially selected in the trachea. Region growing is then performed at this seed point until the entire lungs are segmented. This region growing involves a high threshold in order to fill the lungs via the airways. Dilation followed by erosion is then performed on the segmented image to fill empty spaces caused by fluid-filled regions such as vessels. The erosion operator is slightly larger than the dilation operator to prevent the ribs and other structures near the chest wall from being included in the mask. Lung vessels are then segmented by including all voxels above a threshold value within the lung mask. The threshold is selected to include vessels both with and without contrast, since the presence of PE will block the flow of the contrast to some vessels. Next a connected-component labeling is performed on the segmented structures. Structures with small volume are eliminated. The result is a segmentation of the pulmonary vasculature S. A limitation of this process is that pulmonary veins or other dense structures may be included along with arteries. The resulting segmentation S is shown in FIG. 3 as 300. The segmentation 300 shows an outline of the lungs 302 as well as the vasculature 304.

Any other known method may also be used to produce the segmentation. For example, a line filter, as described in Sato Y, et al., "Three-dimensional multi-scale line filter for segmentation and visualization of curvilinear structures in medical images," Medical Image Analysis, vol. 2, no. 2, pp 143-168 (1998) may also be used. In addition, tree analysis on the line filter output may be used for increased accuracy.

After generation of the segmentation, a signed distance map $D_S$ is computed for the lung vessels. $D_S$ gives the distance of each voxel within S to the closest surface point. Larger arteries will have larger $D_S$ values at their core since they have larger radii. This information is used to compute the sub-tree as described in further detail below.

Step 206 (FIG. 2) represents the identification of the PE site p within the segmented lung vasculature. Such a PE site is shown in FIG. 3 as point 306. This point may be manually identified and indicated (e.g., by a physician), or it may be the output of an automatic detection algorithm. In either case, step 206 represents that the PE site p is an input to the processing steps. Input of the PE site may be, for example, via I/O 108 (if manually identified) or via interface 106 (if automatically identified).

At this point in the processing, the following data is available:
a) the original contrast-enhanced CT image I;
b) segmentation of the lung vessels S containing distance labels $D_S$; and
c) point p within the segmented image for further analysis.

Figure 4:
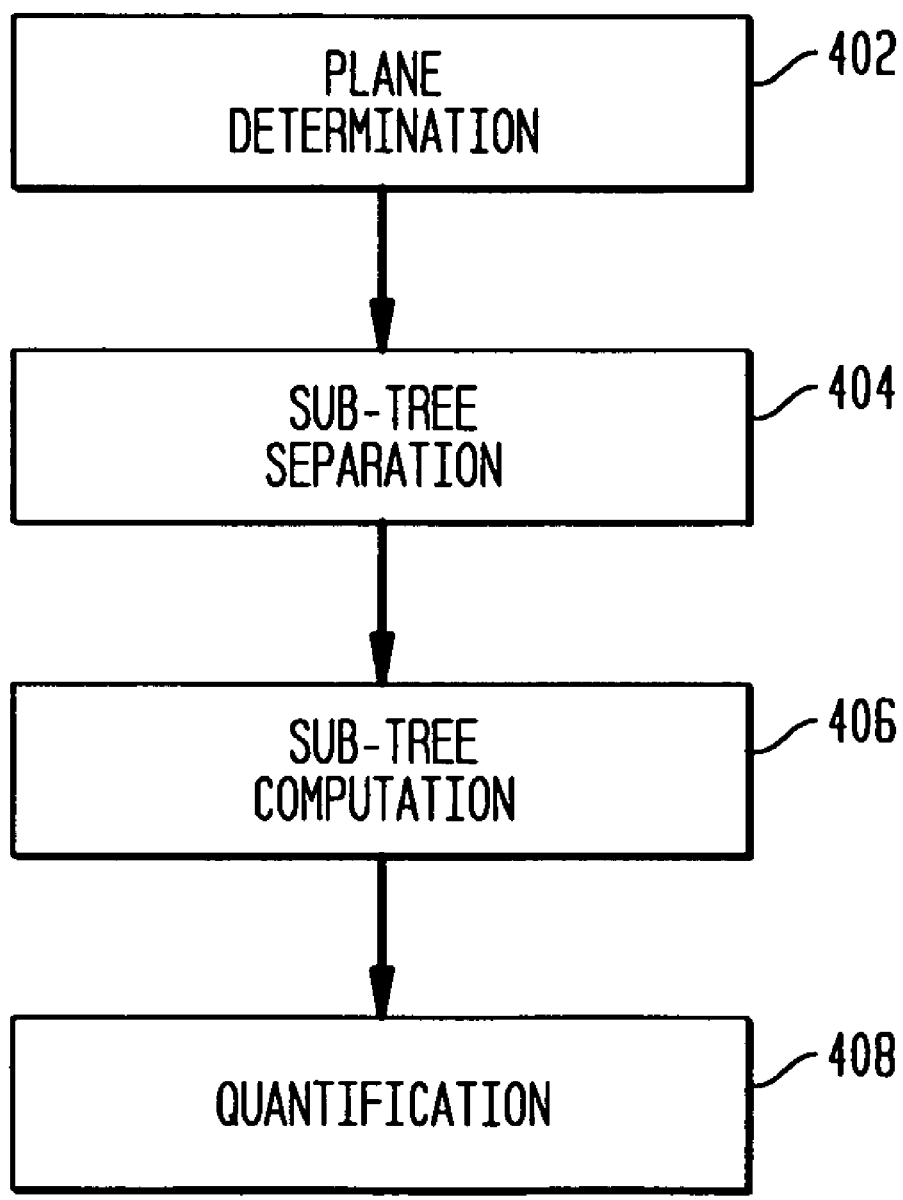
FIG. 4 is a flowchart of the steps performed during the analysis of the arterial sub-tree affected by the PE.

At this point, the process may proceed with step 208, the analysis of the arterial sub-tree affected by the PE. In this step, the sub-tree affected by the PE is analyzed in order to determine the volume of the lung affected by the embolism. Processing in accordance with step 208 is further described in conjunction with the flowchart of FIG. 4. The sub-tree analysis step is comprised of four steps (402-408) as shown in FIG. 4. First, in step 402, a bisecting plane perpendicular to the vessel's direction is determined at the point p. This plane is used to perform a constrained region growing in step 404 to isolate the distal portion of the tree, which is referred to as the sub-tree. In step 406 a tree model is calculated from the sub-tree via a skeletonization-based method, and analyzed to eliminate intersecting vessels. In step 408, the affected lung volume is determined. Further detail of each of the steps of FIG. 4 is described below.

Figure 5:
FIG. 5 shows the organ vasculature with the identified perpendicular plane of intersection with the selected PE point.

Step 402 determines a perpendicular plane of intersection with the selected PE point on the vessel. This plane is illustrated in FIG. 5 as plane 502, with the PE point illustrated as 504. In accordance with this step, given the selected point p 504, a fixed-size sub-volume of the segmentation S is created about p. Note that this fixed-size sub-volume only contains the local tree structure and not the complete tree in either proximal or distal directions. The segmented vasculature within this sub-volume is then modeled by a known skeletonization-based tree computation method. This skeletonization-based tree computation method is described in detail in, A. P. Kiraly, et al., "Three-Dimensional Path Planning for Virtual Bronchoscopy," IEEE Transactions on Medical Imaging, Vol. 23, No. 9, pp. 1365-1379, September 2004, which is incorporated herein by reference. This method is generally described herein as follows.

Figure 6:
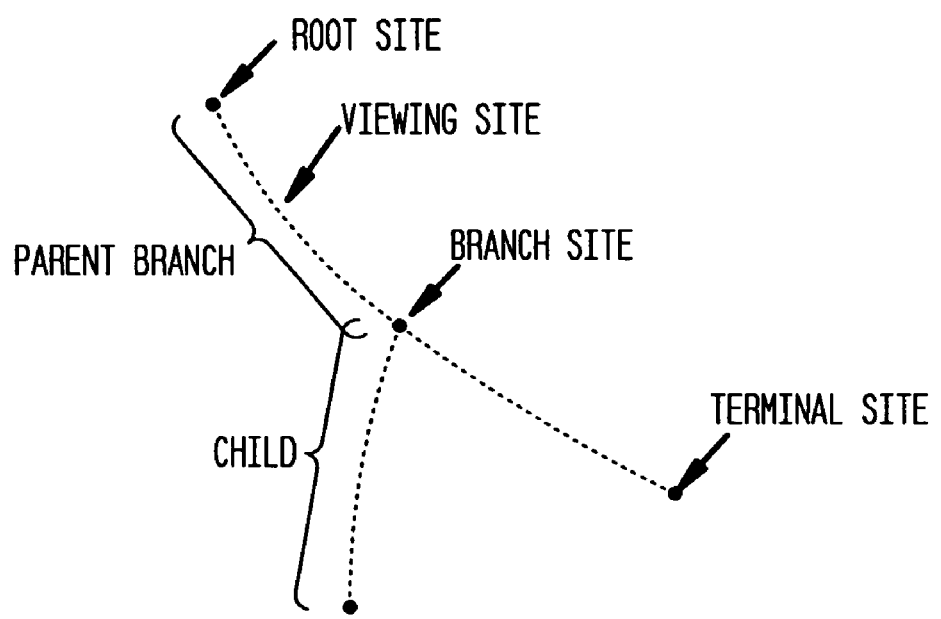
FIG. 6 shows a tree model.

The tree computation method computes a tree model given a segmented image of vasculature and a root site. A simple tree model is shown in FIG. 6. The tree is composed of a series of connected branches. Each branch, in turn, is composed of a series of sites. The root site defines the root of the tree and determines the parent-child relationships for all branches. The branch site is the site where branching occurs between two branches. Terminal sites are found at the end points of branches without children. Finally, all other sites are called viewing sites.

The following procedure is used to determine the tree model. Given a segmented structure, its 3D skeleton is first computed. This operation converts the segmentation into a one-voxel thick structure composed of branching 3D lines. The skeleton is then stored into a tree model format where branches and branch points are found. The root site determines the root of the tree. The sites of each branch are the voxel locations forming a branch. This initial tree model most likely contains false branches due to the discrete nature of the data and the roughness of the segmentation. Using size-based criteria, false branches are deleted to refine the model. The site locations are also refined to a sub-voxel level. Finally, each site of the remaining branches also gets assigned a direction perpendicular to the branch direction on the basis of the locations of neighboring sites.

The above described method is applied to the sub-volume obtained about point p. Our interest is in acquiring the perpendicular plane at location p. The root site is simply chosen as the point within the segmentation furthest from p. Note that this root site may be incorrect with regard to the distal and proximal portions of the tree. The true root site should be located at the most proximal branch of the tree. However, the root site location does not influence the computed perpendicular plane at location p. Given the computed model, we take the site closest to p and take the viewing direction of that site as perpendicular to the plane.

Figure 7:
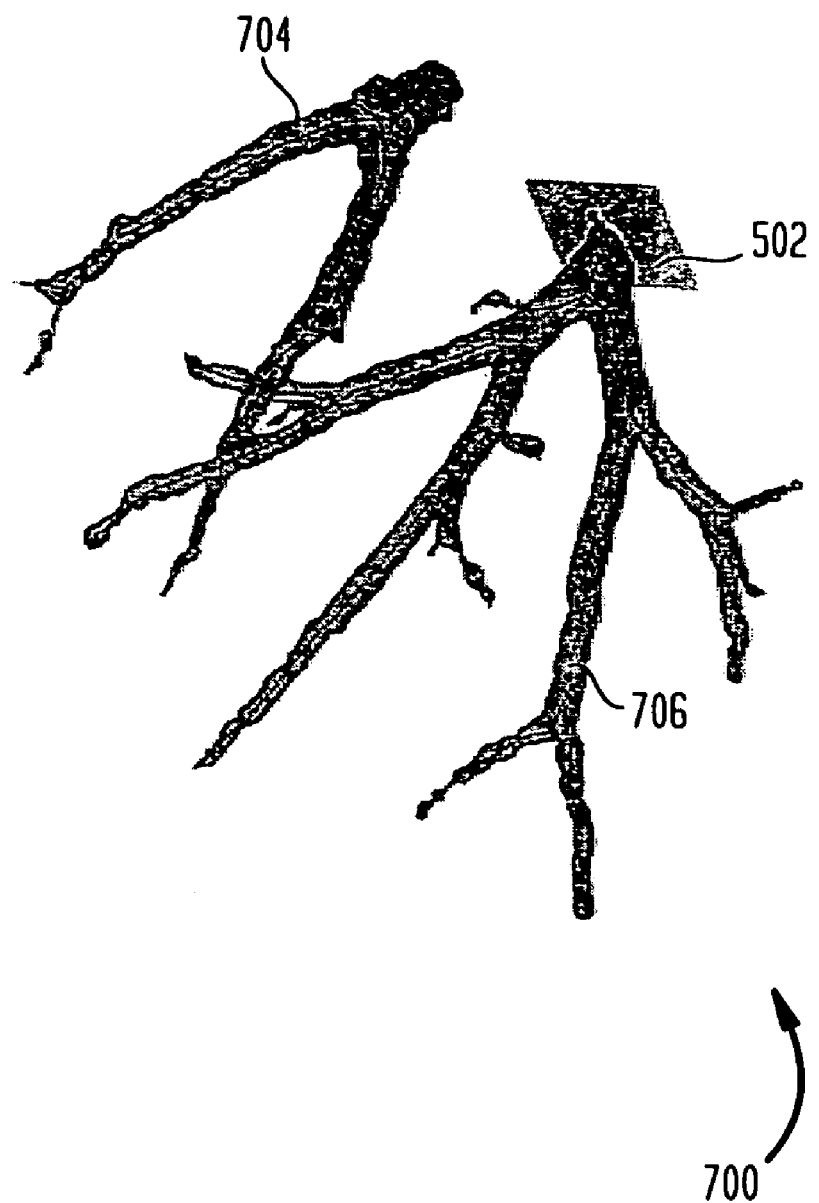
FIG. 7 shows a segmentation of the distal portion of the selected vasculature.

The next step (404 FIG. 4) uses this defined plane to cut the sub-tree from the rest of the tree. Step 404 proceeds as follows. Given the plane 502 that bisects the vessel, there is still the question of which side of the tree contains the sub-tree of interest and which side contains the proximal vessels towards the heart. The purpose of this step is to produce the segmentation of the distal portion of the selected vasculature, which is referred to as S'. Two rule-based region-growing operations are performed on the segmented structure S at the location p, one on each side of the plane. A standard 3D region growing operation is performed that is constrained in two ways. First, it must be bound by the segmentation defined in S. Second, the region may not cross the previously defined plane 502. The smaller of the two regions is taken as the distal tree. The end result is a determination of the distal sub-tree $S' \subset S$, which is the basis for further processing. This distal sub-tree S' is shown in FIG. 7 as 700. Note that this sub-tree may include additional vessels 704 that appear to intersect due to partial volume effects. These intersecting additional vessels are addressed in the next step.

In step 406 a tree model is calculated from the sub-tree via a skeletonization-based method (as directed above), and analyzed to eliminate intersecting vessels. Given the sub-tree S' 700, its tree structure is determined by the skeletonization-based tree computation method described above in connection with step 402. This skeletonization-based tree is shown in FIG. 7 as a line within the vessels (e.g., 706). As discussed above, step 402 only computed the tree structure about the selected point p, not the entire sub-tree. The goal of step 406 is to provide a model of the sub-tree. The branch end point closest to the selected point p is automatically chosen as the root site for the model. However, the tree computation method assumes that the segmented tubular structure given as input forms a true vessel tree and contains no overlapping structures. This is not the case with all given sub-trees since the vessels of the lungs may contain apparent overlaps due to partial volume effects. Hence, the computed model will contain incorrect branches into nearby vascular trees whenever such trees cross in S'.

Figure 8:
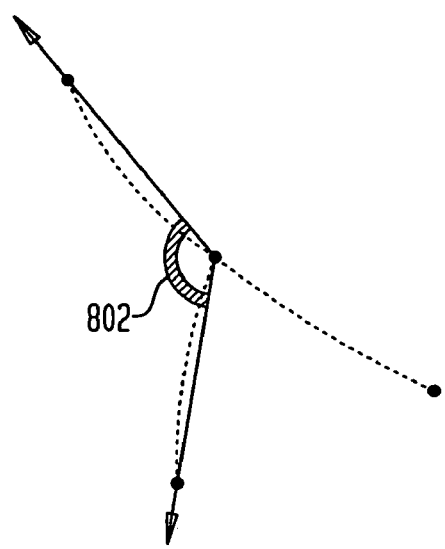
FIG. 8 illustrates a branch angle.
Figure 9:
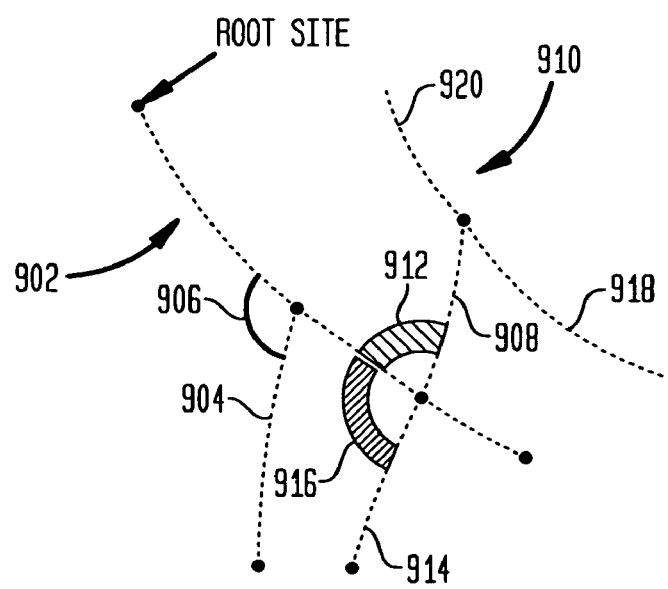
FIG. 9 illustrates a method for determining intersecting branches using branch angle analysis.

Given the tree model of the segmentation, it is possible to determine vessel intersections due to nearby vessels. First, the branch angles 802 of each branch are determined, as shown in FIG. 8. FIG. 9 illustrates a method to identify and eliminate crossing vessels. The distal arterial tree 902 has a branching structure that produces, in general, branch angles of greater than 90 degrees from the parent branch. For example, child branch 904 has a branch angle 906 of greater than 90 degrees. Now consider vessel 908 of sub-tree 910 that intersects within S', and is therefore captured in the tree structure. This intersection will produces a branch angle 912 that is less than 90 degrees, along with a sibling branch 914 having a supplementary branch angle 916 (a margin of error is allowed for angles to be considered supplementary). Thus, in accordance with step 406, crossing vessels are identified by 1) a child branch having an acute branch angle with respect to the parent branch; and 2) a sibling branch having a supplementary branch angle. Thus, in accordance with this test, branches 908 and 914 are identified as an intersecting vessel. Identified crossing branches are eliminated from the model. Note that the elimination of a branch from the tree model also requires the elimination of all of the branches that had been captured into the model as its descendents. Thus, in the example of FIG. 9, parent branch 908 as well as branch 918 will also be eliminated since with respect to the root site, the tree structure models them as descendents of branch 908. The identification and deletion proceeds in an iterative fashion until the entire attached tree structure of the intersecting vessel is eliminated from the model.

Figure 10:
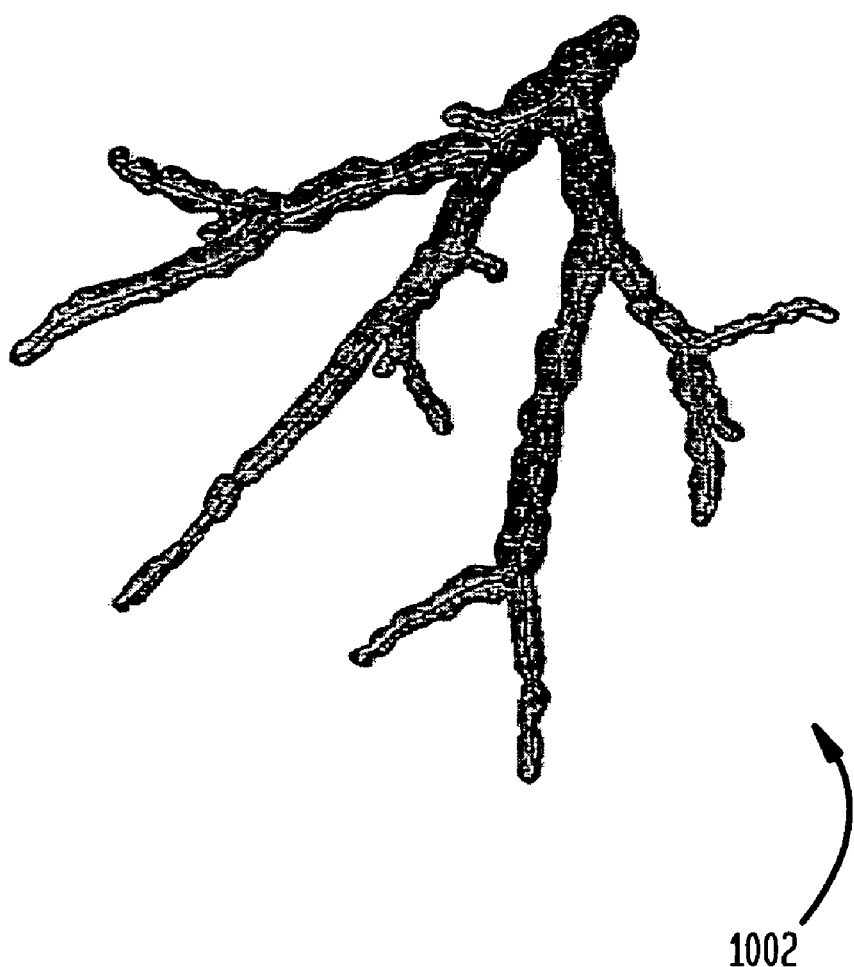
FIG. 10 shows a tree model and segmentation with intersections removed.

The final tree model and segmentation without any intersections is shown in FIG. 10 as 1002, and can be used to refine the vessel sub-tree defined in S'. Every site of every branch is associated with a distance value through $D_S$. As described above, the distance values give the value of the shortest path from a given segmented voxel to the surface of the vessel.

Hence, the value is the radius of the largest sphere that can be contained within the segmentation at a particular voxel location. The availability of these distance values allows the tree model to recreate S' by placing appropriately sized spheres at each site in the tree model and capturing the portion of S that intersects these spheres. Since intersecting trees are eliminated from the model, they will not appear in this recreated S'. The final S' then only contains the vessel sub-tree without intersections as shown in FIG. 10. Hence, the initial determination of S' is not final and is further improved through high-level information available though the tree model.

At this point, step 408 may proceed to quantify the lung volume affected by the PE. This quantification step 408 estimates the region of the lung volume that is perfused by the sub-tree. In order to more accurately estimate this region, a detailed sub-tree involving the vessels near the chest wall is necessary. Although high resolution CT allows the extraction of small vessels, in most cases the segmented tree will not reach the chest wall. However, the segmentation comes sufficiently close to the wall to allow a good approximation of the affected volume.

Figure 11:
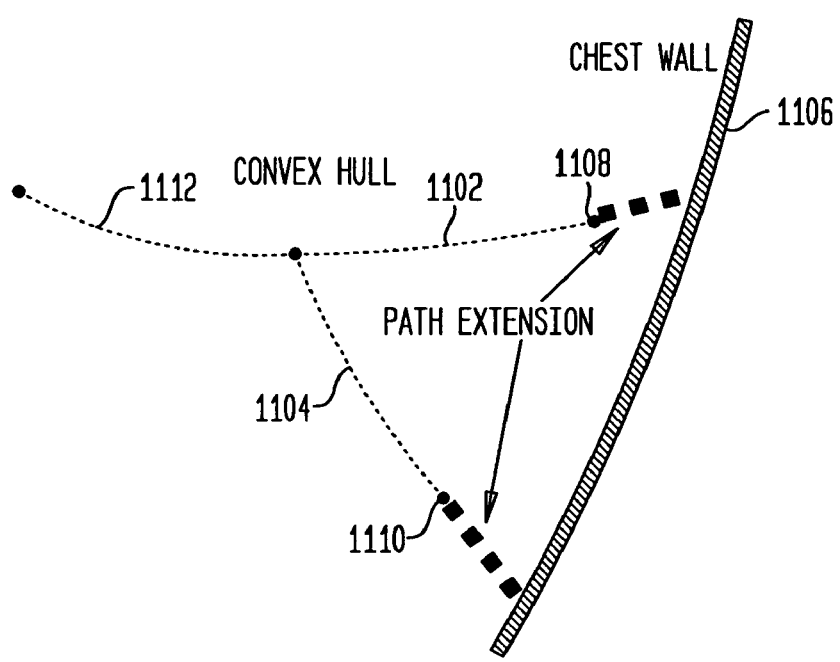
FIG. 11 illustrates extension of terminal branches of a tree.

As illustrated in FIG. 11, each terminal branch (i.e., a branch with no children) (1102, 1104) in the tree model is linearly extended until it touches the edges of the lungs at the chest wall 1106. As described above, each site has a viewing direction associated with it, which defines the direction of the vessel at that point. The viewing direction at each terminal site (1108, 1110) of each terminal branch determines the direction of extension.

In order to determine the affected lung volume, a 3 dimensional convex hull 1112 of the extended tree is calculated in a well known manner. This convex hull 1112 defines the affected lung region. The volume of this region is then measured (by counting the number of voxels in the convex hull) and divided by the volume of the entire lung (computed by counting the number of voxels within the lung mask) to give a percentage of the lung that is affected. The extension of the branches as described above is an acceptable estimation since the branches are already near the chest wall. Any further branching most likely does not cross outside of the convex hull.

Figure 12:
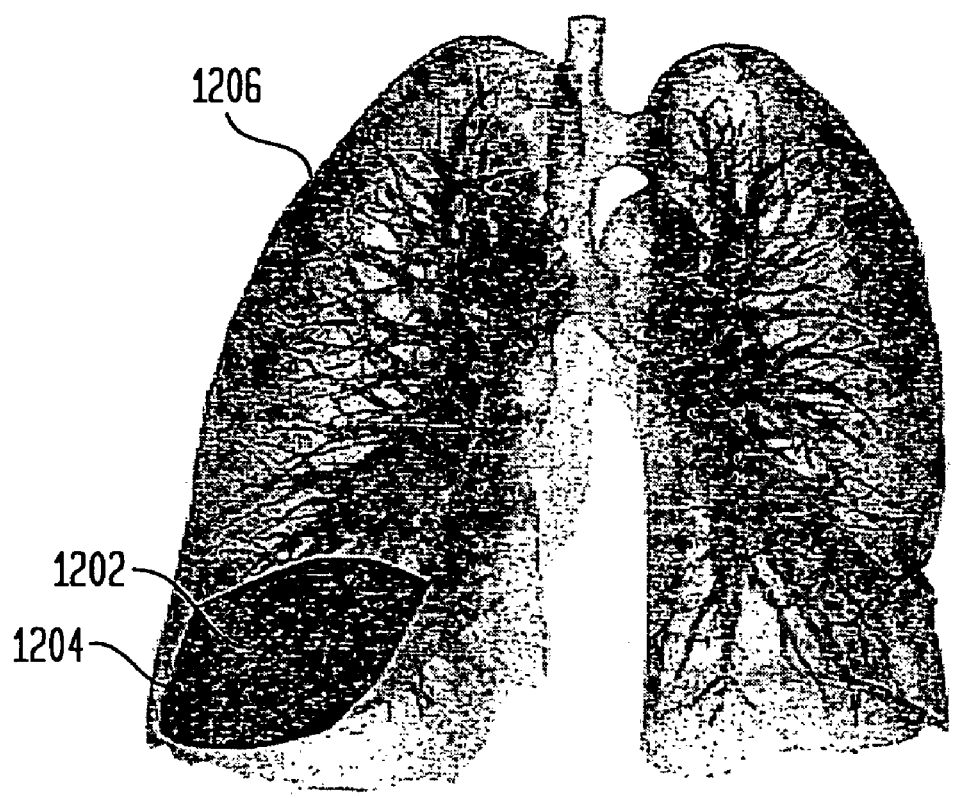
FIG. 12 shows a display of the affected volume of the organ.

The images generated by the above described technique may be displayed to a user via I/O 108 (FIG. 1) (e.g., a computer display monitor) to give graphical feedback of the results of the segmentation and quantification. In an advantageous embodiment, as shown in FIG. 12, the segmented arteries 1202 may be displayed in a transparent color and the convex hull 1204 of the sub-segmented tree is used to visualize the affected region. Further, a transparent view of the lung 1206 provides a visual display of the affected volume of the lung.

For clarity, the above described embodiment was described in connection with a single PE site and the extracted sub-tree. However, some patients have multiple emboli. The above described steps may be repeated for additional selected PE sites, with a new sub-tree extracted for each site. The volumes subtended by each of the sub-trees may be summed together to indicate the total affected lung volume. In the case where an indicated PE is directly downstream of another PE, one sub-tree will be completely contained within another. This condition may be detected from the tree computation. In this case, the volume of the smaller tree is not added to the larger tree when computing the total affected region.

It is noted that in some cases, a pulmonary embolus only partially blocks an artery. In such cases, blood may still flow past the clot, allowing the affected sub-region to be partially perfused with blood. In these cases, it is especially useful to be able to compute the degree to which the lungs are affected by the embolus. The following embodiment estimates the effects of partially occluding emboli. Given the PE site and the segmented vessels, the clot is segmented from the artery in order to calculate its cross-sectional area $A_C$ perpendicular to the segmented vessel. $A_V$, the cross-sectional area of the vessel in which the clot occurs, is also computed from the vessel segmentation. The percentage occlusion is computed as the maximum value of $A_C/A_V$. The degree of effect on the lung is the affected sub-region scaled by the percentage occlusion. In the example shown in FIG. 12, if the percentage occlusion is 80%, then the degree of effect on the lung is 4.6%, or 80% of 5.7%.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention. For example, the present invention was described herein using pulmonary embolism as an illustrative embodiment. However, the present invention is not limited to pulmonary embolism, and is applicable to any type of embolism. Further, the description used CT data as an illustrative embodiment. However the invention is applicable to any type of 3 dimensional medical image data, such as magnetic resonance.

The invention claimed is:

1. An automated method for analyzing the affected region due to an embolism in an organ comprising the steps of:
   generating a segmented image of the organ vasculature using image volume data;
   identifying an embolus point within said segmented image; and
   automatically determining a volume of the organ affected by said embolism,
   wherein said step of automatically determining a volume of the organ affected by said embolism further comprises the step of:
   computing a sub-tree within said segmented image,
   wherein said sub-tree image comprises a plurality of overlapping trees due to nearby vessels in said image, said method further comprising the steps of:
   identifying said overlapping trees; and
   removing said overlapping trees from said sub-tree, and
   wherein said step of identifying overlapping trees further comprises the step of:
   analyzing branch angles within said sub-tree image.

2. The method of claim 1 wherein said step of identifying overlapping trees further comprises the step of:
   identifying overlapping vessels if a child branch has an acute branch angle along with a sibling branch having a supplementary branch angle.

3. An automated method for analyzing the affected region due to an embolism in an organ comprising the steps of:
   generating a segmented image of the organ vasculature using image volume data;
   identifying an embolus point within said segmented image; and
   automatically determining a volume of the organ affected by said embolism, wherein said step of automatically determining a volume of the organ affected by said embolism further comprises the step of:
   computing a sub-tree within said segmented image, and
wherein said step of determining a volume of the organ affected by said embolism further comprises the step of:
   calculating a volume of a region of said organ that is perfused by said sub-tree.

4. The method of claim 3 wherein said organ is a lung.

5. The method of claim 3 wherein said step of identifying an embolus point comprises receiving said embolus point as input from a user.

6. The method of claim 3 wherein said step of identifying an embolus point comprises automatically identifying said embolus point.

7. The method of claim 3 wherein said image volume data comprises computed tomography data.

8. The method of claim 3 wherein said step of automatically determining a volume of the organ affected by said embolism further comprises the step of:
   scaling the volume of the organ affected by said embolism based on a percentage occlusion of a partial embolus.

9. The method of claim 3 wherein said step of computing a sub-tree within said segmented image further comprises the step of:
   identifying vessels that are distal to said embolus point.

10. The method of claim 3 wherein said step of computing a sub-tree within said segmented image further comprises the step of:
   determining a plane perpendicular to a vessel at said embolus point;
   wherein said sub-tree comprises a distal portion of said vasculature with respect to said plane.

11. The method of claim 3 wherein said sub-tree image comprises a plurality of overlapping trees due to nearby vessels in said image, said method further comprising the steps of:
   identifying said overlapping trees; and
   removing said overlapping trees from said sub-tree.

12. The method of claim 3 wherein said step of calculating a volume of said organ that is perfused by said sub-tree further comprises the steps of:
   generating an extended sub-tree by extending terminal branches of said sub-tree to an edge of said organ; and
   computing a convex hull of said extended sub-tree.

13. Apparatus for analyzing the affected region due to an embolism in an organ comprising:
   means for generating a segmented image of the organ vasculature using image volume data;
   means for identifying an embolus point within said segmented image; and
   means for automatically determining a volume of the organ affected by said embolism,
   wherein said means for automatically determining a volume of the organ affected by said embolism further comprises:
      means for computing a sub-tree within said segmented image,
   wherein said sub-tree image comprises a plurality of overlapping trees due to nearby vessels in said image, said apparatus further comprising:
      means for identifying said overlapping trees; and
      means for removing said overlapping trees from said sub-tree, and
   wherein said means for identifying overlapping trees further comprises:
      means for analyzing branch angles within said sub-tree image.

14. The apparatus of claim 13 wherein said means for identifying overlapping trees further comprises:
   means for identifying overlapping vessels if a child branch has an acute branch angle along with a sibling branch having a supplementary branch angle.

15. Apparatus for analyzing the affected region due to an embolism in an organ comprising:
   means for generating a segmented image of the organ vasculature using image volume data;
   means for identifying an embolus point within said segmented image; and
   means for automatically determining a volume of the organ affected by said embolism,
   wherein said means for automatically determining a volume of the organ affected by said embolism further comprises:
      means for computing a sub-tree within said segmented image, and
   wherein said means for determining a volume of the organ affected by said embolism further comprises:
      means for calculating a volume of a region of said organ that is perfused by said sub-tree.

16. The apparatus of claim 15 wherein said means for identifying an embolus point comprises means for receiving said embolus point as input from a user.

17. The apparatus of claim 15 wherein said means for identifying an embolus point comprises means for automatically identifying said embolus point.

18. The apparatus of claim 15 wherein said image volume data comprises computed tomography data.

19. The apparatus of claim 15 wherein said means for automatically determining a volume of the organ affected by said embolism further comprises:
   means for scaling the volume of the organ affected by said embolism based on a percentage occlusion of a partial embolus.

20. The apparatus of claim 15 wherein said means for computing a sub-tree within said segmented image further comprises:
   means for identifying vessels that are distal to said embolus point.

21. The apparatus of claim 15 wherein said means for computing a sub-tree within said segmented image further comprises:
   means for determining a plane perpendicular to a vessel at said embolus point;
   wherein said sub-tree comprises a distal portion of said vasculature with respect to said plane.

22. The apparatus of claim 15 wherein said sub-tree image comprises a plurality of overlapping trees due to nearby vessels in said image, said apparatus further comprising:
   means for identifying said overlapping trees; and
   means for removing said overlapping trees from said sub-tree.

23. The apparatus of claim 15 wherein said means for calculating a volume of said organ that is perfused by said sub-tree further comprises:
   means for generating an extended sub-tree by extending terminal branches of said sub-tree to an edge of said organ; and
   means for computing a convex hull of said extended sub-tree.

24. A computer readable medium comprising stored computer program code for analyzing the affected region due to an embolism in an organ, said computer program code, when executed by a processor, defining the steps of:
- generating a segmented image of the organ vasculature using image volume data;
- identifying an embolus point within said segmented image; and
- automatically determining a volume of the organ affected by said embolism,
- wherein said computer program code defining the step of automatically determining a volume of the organ affected by said embolism further comprises computer program code defining the step of:
- computing a sub-tree within said segmented image,
- wherein said sub-tree image comprises a plurality of overlapping trees due to nearby vessels in said image, said computer readable medium further comprising computer program code defining the steps of:
- identifying said overlapping trees; and
- removing said overlapping trees from said sub-tree, and
- wherein said computer program code defining the step of identifying overlapping trees further comprises computer program code defining the step of:
- analyzing branch angles within said sub-tree image.

25. The computer readable medium of claim 24 wherein said computer program code defining the step of identifying overlapping trees further comprises computer program code defining the step of:
- identifying overlapping vessels if a child branch has an acute branch angle along with a sibling branch having a supplementary branch angle.

26. A computer readable medium comprising stored computer program code for analyzing the affected region due to an embolism in an organ, said computer program code, when executed by a processor, defining the steps of:
- generating a segmented image of the organ vasculature using image volume data;
- identifying an embolus point within said segmented image; and
- automatically determining a volume of the organ affected by said embolism,
- wherein said computer program code defining the step of automatically determining a volume of the organ affected by said embolism further comprises computer program code defining the step of:
- computing a sub-tree within said segmented image, and
- wherein said computer program code defining the step of determining a volume of the organ affected by said embolism further comprises computer program code defining the step of:
- calculating a volume of a region of said organ that is perfused by said sub-tree.

27. The computer readable medium of claim 26 wherein said computer program code defining the step of identifying an embolus point comprises computer program code defining the step of receiving said embolus point as input from the user.

28. The computer readable medium of claim 26 wherein said computer program code defining the step of identifying an embolus point comprises computer program code defining the step of automatically identifying said embolus point.

29. The computer readable medium of claim 26 wherein said image volume data comprises computed tomography data.

30. The computer readable medium of claim 26 wherein said computer program code defining the step of automatically determining a volume of the organ affected by said embolism further comprises computer program code defining the step of:
- scaling the volume of the organ affected by said embolism based on a percentage occlusion of a partial embolus.

31. The computer readable medium of claim 26 wherein said computer program code defining the step of computing a sub-tree within said segmented image further comprises computer program code defining the step of:
- identifying vessels that are distal to said embolus point.

32. The computer readable medium of claim 26 wherein said computer program code defining the step of computing a sub-tree within said segmented image further comprises computer program code defining the step of:
- determining a plane perpendicular to a vessel at said embolus point;
- wherein said sub-tree comprises a distal portion of said vasculature with respect to said plane.

33. The computer readable medium of claim 26 wherein said sub-tree image comprises a plurality of overlapping trees due to nearby vessels in said image, said computer readable medium further comprising computer program code defining the steps of:
- identifying said overlapping trees; and
- removing said overlapping trees from said sub-tree.

34. The computer readable medium of claim 26 wherein said computer program code defining the step of calculating a volume of said organ that is perfused by said sub-tree further comprises computer program code defining the steps of:
- generating an extended sub-tree by extending terminal branches of said sub-tree to an edge of said organ; and
- computing a convex hull of said extended sub-tree.

* * * * *